US012800678B2

(12) United States Patent
Knappe et al.

(10) Patent No.: US 12,800,678 B2
(45) Date of Patent: Nov. 17, 2026

(54) RIGID FLEXIBLE MAGNETIC IMAGING MOUNT

(71) Applicant: FieldLine Inc., Boulder, CO (US)

(72) Inventors: Svenja Knappe, Boulder, CO (US); Orang Alem, Erie, CO (US)

(73) Assignee: FieldLine Inc., Boulder, CO (US)

(*) Notice: Subject to any disclaimer, the term of this patent is extended or adjusted under 35 U.S.C. 154(b) by 0 days.

(21) Appl. No.: 19/316,229

(22) Filed: Sep. 2, 2025

(65) Prior Publication Data

US 2025/0389796 A1 Dec. 25, 2025

Related U.S. Application Data

(63) Continuation of application No. 18/173,575, filed on Feb. 23, 2023, now Pat. No. 12,429,533.

(60) Provisional application No. 63/312,960, filed on Feb. 23, 2022.

(51) Int. Cl.

| | |
|---|---|
| ***G01R 33/00*** | (2006.01) |
| ***A61B 5/245*** | (2021.01) |
| *A61B 5/369* | (2021.01) |

(52) U.S. Cl.

CPC ............ *G01R 33/007* (2013.01); *A61B 5/245* (2021.01); *G01R 33/0047* (2013.01); *G01R 33/0094* (2013.01); *A61B 5/369* (2021.01)

(58) Field of Classification Search

CPC .............. A61B 2034/301; A61B 5/245; G01R 33/0047; G01R 33/0094; G01R 33/007

See application file for complete search history.

(56) References Cited

U.S. PATENT DOCUMENTS

| | | | |
|---|---|---|---|
| 6,370,414 B1 | 4/2002 | Robinson | |
| 7,107,624 B2 | 9/2006 | Dobbie et al. | |
| 8,768,427 B2 | 7/2014 | Sjaaheim et al. | |
| 8,954,129 B1 | 2/2015 | Schlegel et al. | |
| 9,395,425 B2 | 7/2016 | Diamond et al. | |
| 11,523,776 B2 | 12/2022 | Kim et al. | |
| 2009/0149736 A1 | 6/2009 | Skidmore et al. | |
| 2011/0077490 A1 | 3/2011 | Simpson et al. | |
| 2012/0046531 A1 | 2/2012 | Hua | |
| 2015/0289788 A1 | 10/2015 | Simpson et al. | |
| 2020/0057115 A1 | 2/2020 | JimEnez-Martínez et al. | |
| 2020/0088811 A1* | 3/2020 | Mohseni | G01R 33/032 |
| 2021/0015427 A1 | 1/2021 | Shah et al. | |

* cited by examiner

*Primary Examiner* — Gerald Johnson

(57) ABSTRACT

Various embodiments disclosed herein comprise systems and methods to conform magnetic field sensors to a target geometry. In some examples, an apparatus is configured to conform to a target geometry. The apparatus comprises a sensor mount and a sensor array. The sensor mount comprises a flexible state for a first environmental condition and a rigid state for a second environmental condition. The sensor mount transitions from the flexible state to the rigid state when the first environmental condition transitions to the second environmental condition. The sensor mount transitions from the rigid state to the flexible state when the second environmental condition transitions to the first environmental condition. The sensor array is coupled to the sensor mount.

20 Claims, 7 Drawing Sheets

RIGID FLEXIBLE MAGNETIC IMAGING MOUNT

RELATED APPLICATIONS

This U.S. Patent Application is a continuation of U.S. patent application Ser. No. 18/173,575 titled, "RIGID FLEXIBLE MAGNETIC IMAGING MOUNT" which was filed on Feb. 23, 2023 which in turn claims the benefit of and priority to U.S. Provisional Patent Application 63/312,960 titled, "RIGID FLEXIBLE MAGNETIC IMAGING MOUNT" which was filed on Feb. 23, 2022, both of which are hereby incorporated by reference in their entirety into this U.S. Patent Application.

BACKGROUND

Magnetometer systems detect and characterize magnetic fields generated by a magnetic field source. The magnetometer systems measure the field strength and/or direction of the magnetic fields to characterize the sensed fields. Magnetoencephalography (MEG) systems are a type of magnetometer system that measures magnetic fields generated by neuronal activity within a subject's brain to map brain function. MEG systems image brain activity by detecting magnetic fields from neural currents using an array of magnetic sensors placed near the head of a subject and then computing the locations of the neural activity relative to the location of the sensor in a process referred to as source localization. Exemplary magnetic sensors used in the MEG systems include Optically Pumped Magnetometers (OPMs), however other magnetometer types like Superconducting Quantum Interference Devices (SQUIDs) may be used. The data from the sensors along with each sensor location is used to calculate the locations of neuronal signal sources to form MEG images of brain activity. To perform accurate source localization calculations, the location and orientation of the sensors should remain fixed when taking magnetic field measurements.

Some MEG systems have sensors that can move independently and conform to the size and shape of the head. These MEG systems are referred to as on-scalp or conformal MEG. For example, the sensor array may be positioned on a helmet or cap that is placed on a human head so that the sensors contact the surface of the scalp. In conformal MEG systems, the location and orientation information for the sensor array is determined for every subject and every time the sensors are placed on the scalp to allow for accurate source localization of the neural activity in the brain. Since head shape and size varies from person to person, the locations and orientations of the sensors may change when performing conformal MEG on different subjects. Relocating the sensors and identifying their new locations and orientations is a difficult and time-consuming process. Unfortunately, conformal MEG systems do not efficiently conform the sensors to the target's geometry. Moreover, conformal MEG systems do not effectively secure the positions and orientations of the sensors when conformed to the target's geometry.

OVERVIEW

This Overview is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Various embodiments of the present technology relate to solutions for conformal magnetic imaging systems like conformal Magnetoencephalography (MEG) systems. Some embodiments comprise an apparatus configured to conform to a target geometry. The apparatus comprises a sensor mount and a sensor array. The sensor mount comprises a flexible state for a first environmental condition and a rigid state for a second environmental condition. The sensor mount transitions from the flexible state to the rigid state when the first environmental condition transitions to the second environmental condition. The sensor mount transitions from the rigid state to the flexible state when the second environmental condition transitions to the first environmental condition. The sensor array is coupled to the sensor mount.

Some embodiments comprise a method of operating a magnetic sensing system to conform to a target geometry. In some examples, the method comprises placing a sensor mount on a target when the sensor mount is in a flexible state to position sensors mounted to the sensor mount in spatial locations proximate to the target. The method continues by establishing a low-pressure environment in the sensor mount to transition the sensor mount from the flexible state to a rigid state to secure the positions and orientations of the sensors. The method continues by determining the spatial locations of the sensors. The method continues by measuring the field strength of a magnetic field generated by the target. The method continues by establishing an ambient pressure environment in the sensor mount to transition the sensor mount from the rigid state to the flexible state. The method continues by removing the sensor mount from the target.

DESCRIPTION OF THE DRAWINGS

Many aspects of the disclosure can be better understood with reference to the following drawings. The components in the drawings are not necessarily drawn to scale. Moreover, in the drawings, like reference numerals designate corresponding parts throughout the several views. While several embodiments are described in connection with these drawings, the disclosure is not limited to the embodiments disclosed herein. On the contrary, the intent is to cover all alternatives, modifications, and equivalents.

Figure 1:
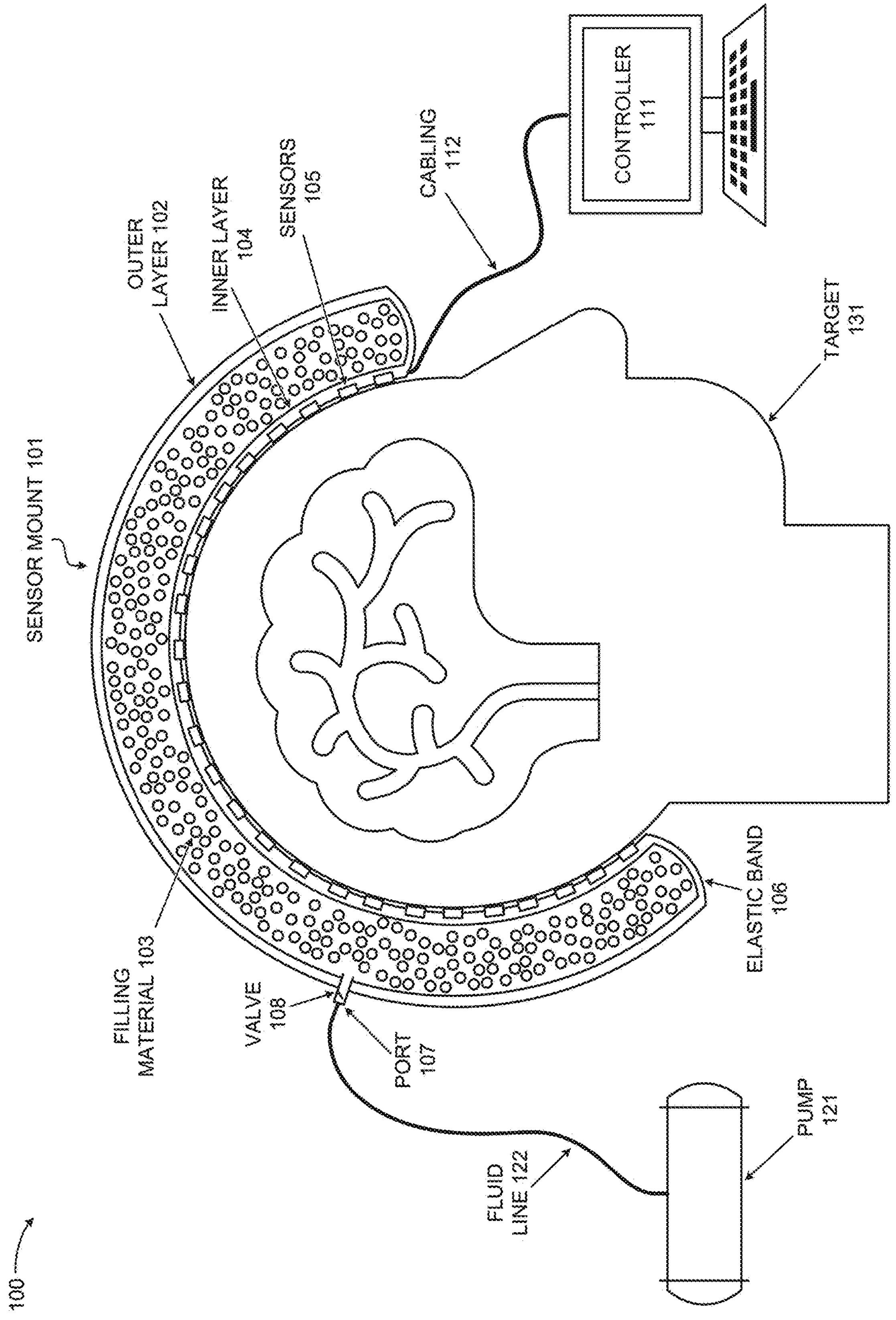
FIG. 1 illustrates an exemplary magnetic imaging system.

The drawings have not necessarily been drawn to scale. Similarly, some components or operations may not be separated into different blocks or combined into a single block for the purposes of discussion of some of the embodiments of the present technology. Moreover, while the technology is amendable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

The following description and associated figures teach the best mode of the invention. For the purpose of teaching inventive principles, some conventional aspects of the best mode may be simplified or omitted. The following claims specify the scope of the invention. Note that some aspects of the best mode may not fall within the scope of the invention as specified by the claims. Thus, those skilled in the art will appreciate variations from the best mode that fall within the scope of the invention. Those skilled in the art will appreciate that the features described below can be combined in various ways to form multiple variations of the invention. As a result, the invention is not limited to the specific examples described below, but only by the claims and their equivalents.

The examples herein present systems and methods to conform magnetic field sensors in conformal magnetic imaging systems like conformal MEG. In the examples of conformal MEG systems provided herein, the sensors, like Optically Pumped Magnetometers (OPMs), are mounted to a rigid/flexible magnetic imaging mount. The imaging mount comprises a flexible state associated with an ambient pressure environment and a rigid state associated with a low-pressure environment. When in its flexible state, the imaging mount is placed on a target and conforms to the target's geometry (e.g., a human head). The imaging mount contacts the sensors to the surface of the target subject in locations proximate to the magnetic field source of the target. The ambient pressure environment is transitioned to the low-pressure environment. In response, the imaging mount transitions to its rigid state. When in the rigid state, the imaging mount secures the positions and orientations of the sensors to inhibit sensor movement during the magnetic imaging process. The sensors measure the strength of magnetic fields that characterize neuronal activity in the target and transfer the sensor data to a controller. When the magnetic field measurements are finished, the low-pressure environment is transitioned to the ambient pressure environment. In response, the imaging mount transitions from its rigid state to its flexible state allowing the imaging mount to be removed from the target. The flexibility of the imaging mount efficiently conforms the sensors to the surface geometry of the target. By efficiently conforming the sensors to the target geometry, the sensors are quickly positioned at spatial locations proximate to the magnetic field source of the target. Moreover, the flexibility of the imaging mount allows the sensors to conform to the surface geometry of the target independent of target shape and size. The rigidity of the imaging mount effectively secures the positions and orientations of the sensors. Securing the positions and orientations of the sensors inhibits sensor movement during magnetic field measurements. By inhibiting sensor movement during magnetic field measurements, the quality and accuracy of the measurements is improved. Furthermore, the ability of the imaging mount to transition between rigid and flexible states allows for the imaging mount to be reused for different targets with different surface geometries. Now referring to the Figures.

FIG. 1 illustrates magnetic imaging system 100 in a cross-sectional view. Magnetic imaging system 100 performs operations like detecting magnetic fields and relating the detected magnetic fields to neuronal activity for use in medical applications. Exemplary medical applications include identifying brain activity and diagnosing medical conditions like stroke, epilepsy, neuronal injuries, neuronal disorders, and/or other types of medical conditions relating to brain/neuron activity. Magnetic imaging system 100 comprises sensor mount 101, controller 111, cabling 112, pump 121, fluid line 122, and target 131. Sensor mount 101 comprises outer layer 102, filling material 103, inner layer 104, sensors 105, elastic band 106, port 107, and valve 108. Controller 111 is coupled to sensor mount 101 via cabling 112. Pump 121 is coupled to sensor mount 101 via fluid line 122. In this example, target 131 comprises a human head however target 131 may comprise any magnetic field source including non-biological magnetic field sources.

Sensor mount 101 is representative of a rigid/flexible cap for conformal magnetic imaging like a conformal MEG cap. Sensor mount 101 comprises a wearable headgear configured to position sensors 105 in spatial locations proximate to target 131. For example, sensor mount 101 may securely adhere sensors 105 to the scalp of target 131. Sensor mount 101 is constructed from a flexible material and is shaped to fit the geometry of target 131. In some examples, sensor mount 101 comprises a chinstrap to fasten it to the head of the target.

Outer layer 102 is coupled to inner layer 104 by elastic band 106. Outer layer 102, inner layer 104, and elastic band 106 form an enclosed region within sensor mount 101. For example, outer layer 102, inner layer 104, and elastic band 106 may comprise an airtight membrane. Filling material 103 is positioned in the enclosed region in the interior of sensor mount 101. Outer layer 102 and inner layer 104 comprise a soft and flexible material like rubber, silicone, neoprene, plastic, cloth, or some other type of suitable material. Outer layer 102, inner layer 104, and elastic band 106 are impermeable to filling material 103 and are impermeable or semi-permeable to fluids like air, oxygen, nitrogen, carbon dioxide, and the like. Elastic band 106 comprises an elastic material like rubber that constricts in response to being stretched. When sensor mount 101 is placed on target 131, elastic band 106 constricts sensor mount 101 inward to conform sensor mount 101 to the shape of target 131 and secure sensor mount 101 to target 131. Port 107 is positioned on outer layer 102. Port 107 bridges outer layer 102 into the enclosed region. Port 107 allows fluid (e.g., air) to pass between the enclosed region and the exterior environment but inhibits the particles that comprise filling material 103 from escaping the enclosed region. For example, port 107 may comprise a screen with a mesh size smaller than the size of the particles that comprise filling material 103 to allow fluid to pass through port 107 and prevent filling material 103 from escaping the enclosed region. Port 107 comprises valve 108. Valve 108 may be toggled between off and on orientations to selectively seal the enclosed region in sensor mount 101.

Sensors 105 are embedded into inner layer 104 of sensor mount 101. For example, inner layer 104 may comprise indentations shaped to hold sensors 105 with mounts to fasten sensors 105 to inner layer 104. The indentations may comprise mechanical holders like clamps, couplers, male/female sockets, screw ports, and the like that bind sensors 105 to inner layer 104. The indentations may comprise adhesives like glue, hook-and-loop fasteners, and the like that bind sensors 105 to inner layer 104. In other examples, the sensors may be secured to the outer layer of the sensor mount in some other way. In this example, sensor mount 101 comprises 25 sensors, however in other examples, sensor mount 101 may comprise a different number of sensors. For example, sensor mount 101 may comprise as many as 150 sensors. A portion of each of sensors 105 is exposed. The exposed section of each of sensors 105 physically contacts the surface of target 131 when sensor mount 101 is worn by target 131. Sensor mount 101 may comprise embedded circuitry that couple sensors 105 to cabling 112.

Filling material 103 comprises a particle matter. The particle matter may comprise glass particles, silicate particles, ceramic particles, plastic particles, a mixture, and/or another type or types of particles that do not interfere in the operation of sensors 105. The size of the particles may be uniform or distributed. The geometric shape of the particles may be uniform, or the shape of the particles may differ from particle-to-particle. For example, the particles may all comprise a spherical shape, or the particles may comprise a mixture of spheroids, prismoids, pyramids, and the like. The average size of the particles allows filling material 103 to flow in a fluid-like state when in a first environmental condition and to solidify in a second environmental condition. For example, filling material 103 may flow in a fluidized manner when under ambient pressure and may solidify when a vacuum is pulled on filling material 103. The number of particles that comprise filling material 103 varies based on the average size of the particles and the volume of the enclosed region, however the number of particles is not limited. When filling material 103 is under ambient conditions (i.e., pump 121 is off), the particles loosely fill the enclosed region and allow sensor mount 101 to be flexible. When filling material 103 is under low pressure conditions (i.e., pump 121 is on), sensor mount 101 compresses reducing the volume of the enclosed region causing the particles of filling material 103 to jam together and form a rigid structure. The rigidity of filling material 103 causes sensor mount 101 to become rigid and secures the positions and orientations of sensors 105.

Pump 121 is coupled to port 107 over fluid line 122. When operating, pump 121 removes fluid from the enclosed region through port 107 to create a low-pressure environment within the enclosed region. Valve 108 in port 107 may be closed to maintain the low-pressure environment within the enclosed region. When not operating, the vacuum is released, and air fills the enclosed region of the sensor mount 101 to create an atmospheric environment in the enclosed region.

Sensors 105 comprise magnetometers that sense magnetic fields generated by a magnetic field source in target 131. Sensors 105 generate signals that characterize the strength of the detected magnetic fields. In this example, the magnetic field source comprises the brain of target 131. The neuronal activity in the brain of target 131 comprises intercellular electromagnetic signals. Sensors 105 sense the magnetic component of the electromagnetic signals to detect neuronal activity. Sensors 105 form a sensor array that is contoured to the head of target 131 by sensor mount 101. Exemplary magnetometers that may comprise sensors 105 include Optically Pumped Magnetometers (OPMs), atomic magnetometers, gradiometers, magnetic gradiometers, nitrogen-vacancy centers, high-temperature Superconducting Quantum Interference Devices (SQUIDs), Electroencephalography (EEG) sensors, functional Near Infrared Spectroscopy (fNIRS), and the like.

Sensors 105 are coupled to controller 111 over cabling 112. Cabling 112 comprises sheathed metallic wires. For example, sensors 105 may transfer signaling that characterizes the sensed magnetic field to controller 111 over cabling 112. In some examples, cabling 112 may be replaced with, or used in addition to, a wireless transceiver system (e.g., antennas) to wirelessly transfer communications between controller 111 and sensors 105 using wireless networking protocol like bluetooth.

Controller 111 is representative of one or more computing devices configured to drive the operation of sensors 105 to generate magnetic images that depict the measured neuronal activity in target 131. The one or more computing devices comprise processors, memories, and transceivers that are connected over bus circuitry. The processors may comprise Central Processing Units (CPUs), Graphical Processing Units (GPUs), Digital Signal Processors (DSPs), Application Specific Integrated Circuits (ASICs), Field Programmable Gate Arrays (FPGAs), and the like. The memories may comprise Random Access Memory (RAM), flash circuitry, Solid State Drives (SSDs), Hard Disk Drives (HDDs), and the like. The memory stores software like operating systems, magnetic imaging applications, localization applications, sensor data, and the like. The processors retrieve and execute the software from the memory to drive the operation of controller 111.

Once sensor mount 101 is in a rigid state and the positions and orientations of sensors 105 are known, controller 111 transfers instructions to sensors 105 that direct sensors 105 to measure a magnetic field generated by neuronal activity in target 131 over cabling 112. Controller 111 receives sensor data from sensors 105 that characterizes the strength and/or other field attributes of the sensed magnetic field. The sensor data may be addressed (e.g., sensor ID) to correlate the measured magnetic field strengths with individual ones of sensors 105. Controller 111 executes a magnetic imaging application (e.g., a MEG application) that performs source localization to generate a magnetic field image (e.g., a MEG image) based on the target magnetic field strengths measured by sensors 105 and the spatial locations for each of sensors 105. The magnetic field image depicts the magnetic field detected by sensors 105 in three dimensions to illustrate the neuronal activity in the brain of target 131.

Various examples of operations and configurations are described herein. In some examples, sensor mount 101 is placed on the head of target 131 and conforms to the geometry of the head of target 131. Sensor mount 101 compresses sensors 105 against the surface of target 131. Pump 121 is activated and draws air out of the enclosed region in sensor mount 101 through port 107. As the air is removed, outer layer 102 and inner layer 104 contact. The contraction causes the particles that comprise filling material 103 to jam together and form a rigid structure. Pump 121 is deactivated. Valve 108 is closed to maintain the low-pressure environment within the enclosed region of sensor mount 101. The rigidity of filling material 103 secures the positions and orientations of sensors 105. Sensors 105 measure the magnetic field generated by neuronal activity in the brain of target 131. Sensors 105 transfer signals that individually characterize the strength of the magnetic field to the controller 111 via cabling 112. Controller 111 receives and processes the signals to model the neuronal activity in the brain of target 131. Fluid line 122 is decoupled from port 107 and valve 108 is opened. Air flows into the enclosed region through port 107 to equalize the internal pressure of sensor mount 101 with the ambient environment. As the air reenters, outer layer 102 and inner layer 104 expand. The expansion causes the particles that comprise filling material 103 to loosen and return to a fluidized state. Sensor mount 101 regains flexibility and is removed from the head of target 131.

Advantageously, sensor mount 101 effectively and efficiently conforms sensors 105 to the surface geometry of target 131 when in a flexible state and secures the positions and orientations of sensors 105 when in a rigid state.

Although the above examples are discussed with relation to magnetic imaging of neuronal activity in the brain, other magnetic imaging modalities are contemplated herein. For example, magnetic imaging system 100 may comprise a Magnetoencephalography (MEG) system, a Magnetocardiography (MCG) system, a Magnetogastrography (MGG) system, a Magnetomyography (MMG) system, or another type of anatomical magnetic sensing technology. Accordingly, the shape of sensor mount 101 may be different than that illustrated in FIG. 1 in the other anatomical magnetic sensing embodiments. For example, when magnetic imaging system 100 comprises an MCG system, sensor mount 101 may comprise a rigid/flexible MCG blanket and/or sensor holder shaped to conform to the chest of a target. For example, when magnetic imaging system 100 comprises a fetal MCG system, sensor mount 101 may comprise a rigid/flexible fetal MCG blanket and/or sensor holder shaped to conform to the chest of an infant or small child. For example, when magnetic imaging system 100 comprises a fetal MEG system, sensor mount 101 may comprise a rigid/flexible fetal MEG cap and/or sensor holder shaped to conform to the head of an infant or small child.

Figure 5:
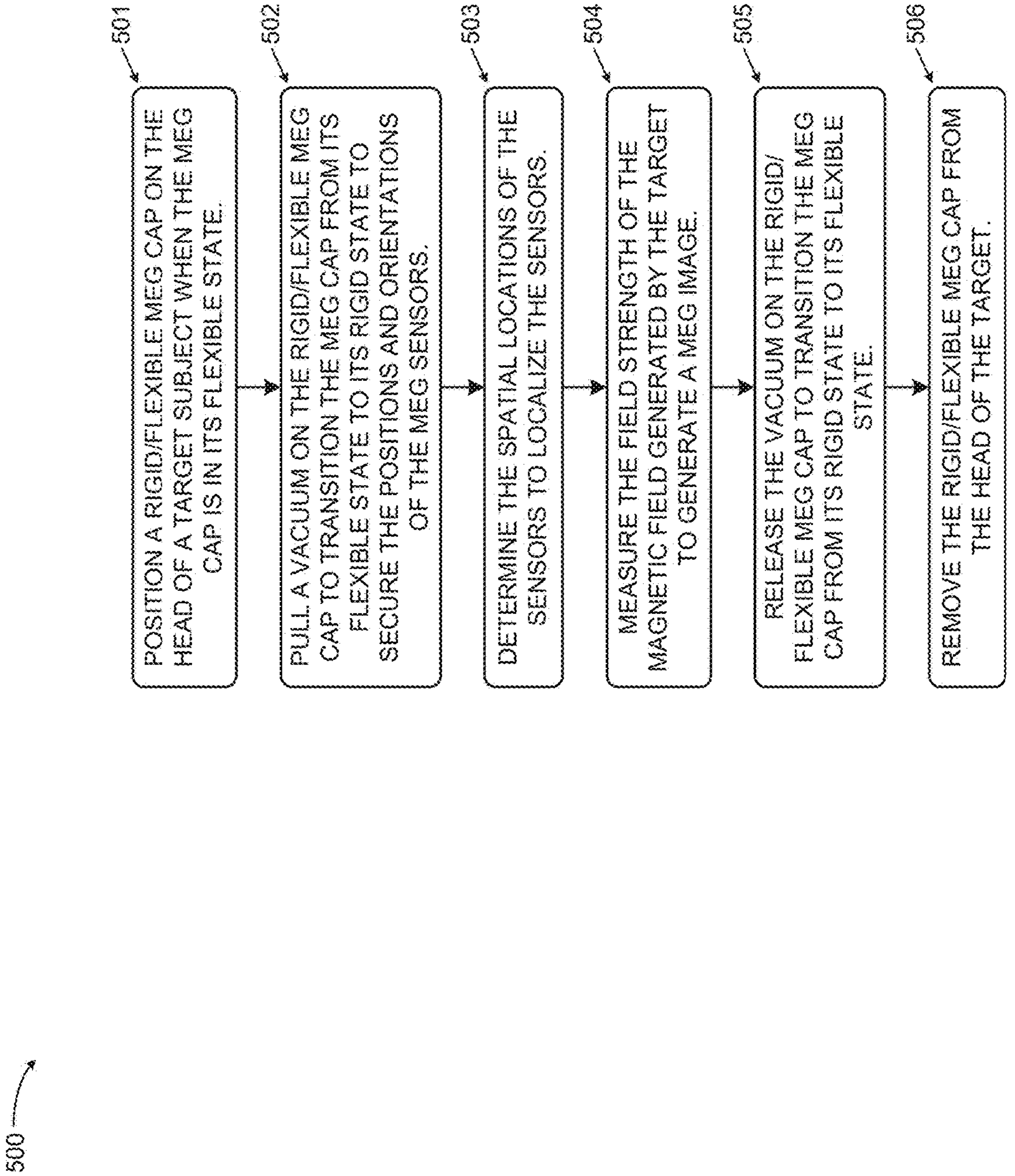
FIG. 5 illustrates an exemplary conformal magnetic imaging process.

In some examples, magnetic imaging system 100 implements process 500 illustrated in FIG. 5. It should be appreciated that the structure and operation of magnetic imaging system 100 may differ in other examples.

Figure 2:
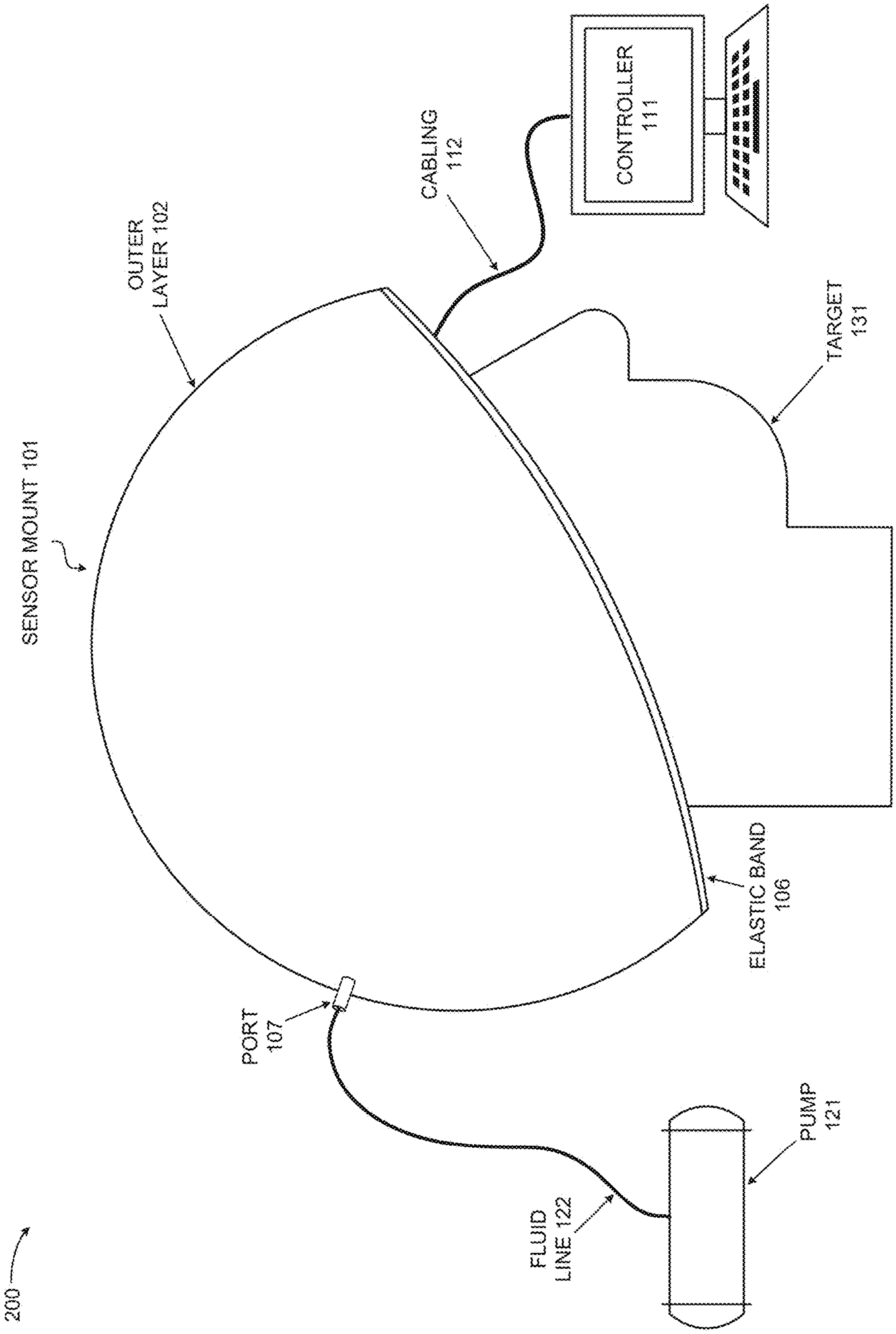
FIG. 2 illustrates an exemplary magnetic imaging system.

FIG. 2 illustrates view 200. View 200 is representative of an external perspective of magnetic imaging system 100. View 200 comprises sensor mount 101, outer layer 102, elastic band 106, port 107, controller 111, cabling 112, pump 121, fluid line 122, and target 131. The view of filling material 103, inner layer 104, and sensors 105 is obstructed by outer layer 102. Sensor mount 101 securely fits onto the head of target 131. When worn by target 131, sensor mount 101 covers the top, sides, front, and back of the scalp while the lower facial extremities of target 131 remain uncovered. In some examples, sensor mount 101 comprises a chin strap that fits below the chin of target 131 and is physically coupled to the sides of sensor mount 101, however the chin strap has been omitted for the sake of clarity. For example, the chin strap may comprise adjustable strapping with hook-and-loop fasteners.

Figure 3:
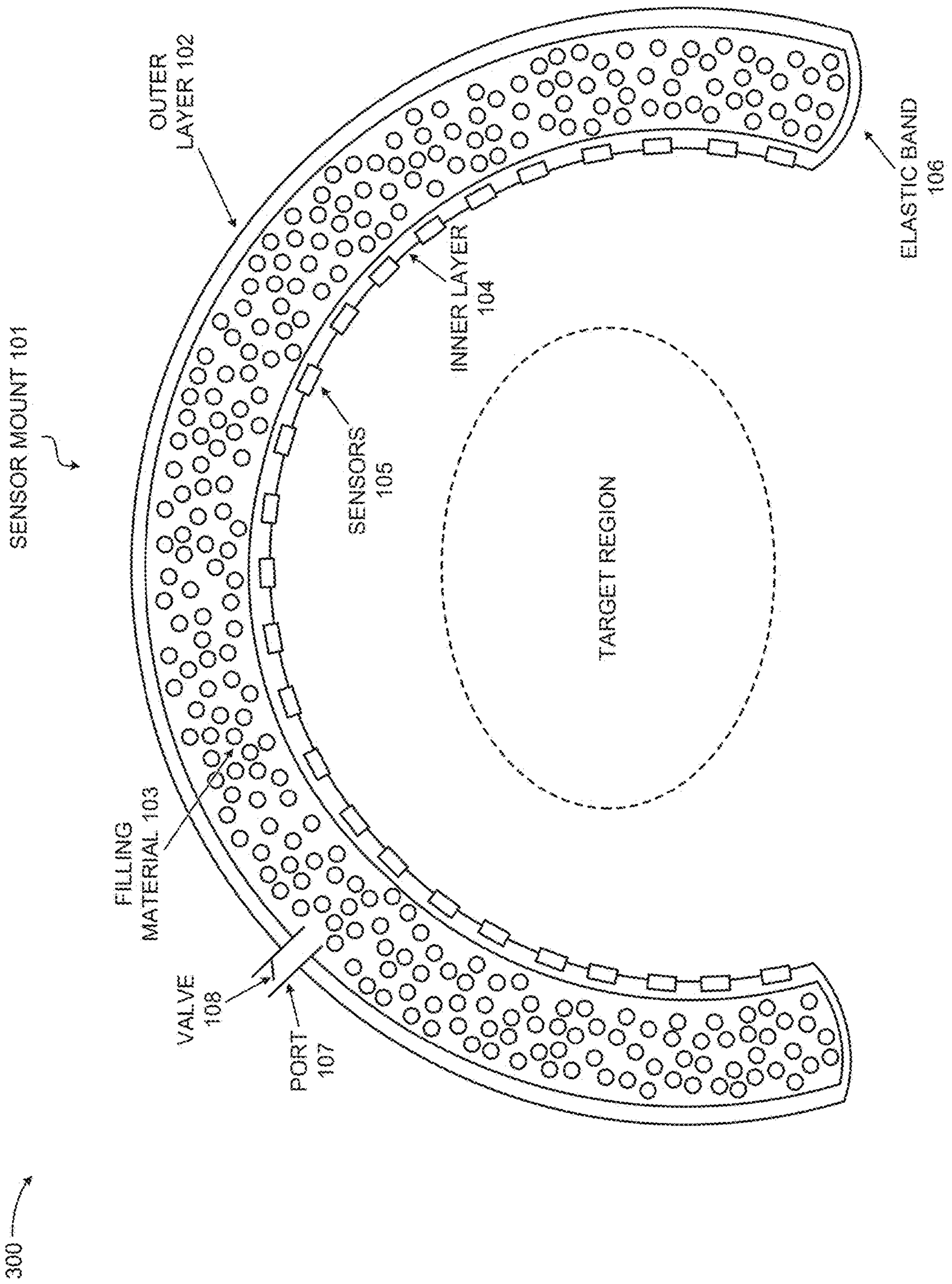
FIG. 3 illustrates an exemplary sensor mount.

FIG. 3 illustrates view 300. View 300 comprises a cross-sectional view of sensor mount 101. View 300 illustrates outer layer 102, filling material 103, inner layer 104, sensor 105, elastic band 106, port 107, and valve 108. Sensor mount 101 is representative of a magnetic imaging cap that comprises a flexible state associated with a first environmental condition and a rigid state associated with a second environmental condition. Sensor mount 101 transitions from the flexible state to the rigid state when the environmental condition associated with the flexible state transitions to the environmental condition associated with the rigid state. Likewise, sensor mount 101 transitions from the rigid state to the flexible state when the environmental condition associated with the rigid state transitions to the environmental condition associated with the flexible state. Elastic band 106 physically couples outer layer 102 to inner layer 104. When sensor mount 101 is in its flexible state and is placed on a target, elastic band 106 constricts inner layer 104 and outer layer 102 to the geometry of the target to secure sensor mount 101 to the target. The constriction presses sensors 105 against the surface of the target. Outer layer 102, inner layer 104, and elastic band 106 form an enclosed region that holds filling material 103. For example, outer layer 102, inner layer 104, and elastic band 106 may comprise a membrane. Filling material 103 comprises particle matter selected for comprising physical properties that cause the particle matter to undergo a reversible jamming transition when the particle density of the filling material exceeds a jamming threshold.

Outer layer 102 comprises port 107. Port 107 crosses outer layer 102 to bridge to enclosed region and the ambient environment. Port 107 may comprise screw couplings, O-rings, gaskets, and the like to couple to a fluid line to remove the interstitial fluid (e.g., air) from the enclosed region. Port 107 comprises valve 108. Valve 108 may open and close port 107 to separate the enclosed region from the ambient environment. For example, air may be pumped out of the enclosed region through port 107 to create a low-pressure environment and valve 108 may be switched to a closed position to maintain the low-pressure environment. Sensors 105 are embedded in inner layer 104 and form a sensor array. Sensors 105 protrude from the outer surface of inner layer 104 in the direction of the target region. When in use, inner layer 104 is positioned towards the target region where the sensors contact the surface of the target. Port 107 forms a channel that allows air to be drawn out of the enclosed region to create a low-pressure environment within the enclosed region of sensor mount 101. When a low-pressure environment is created and sensor mount 101 is placed on the target, filling material 103 becomes rigid and locks the positions and orientations of sensors 105. Sensor mount 101 securely conforms sensors 105 against the surface of the target.

Figure 4:
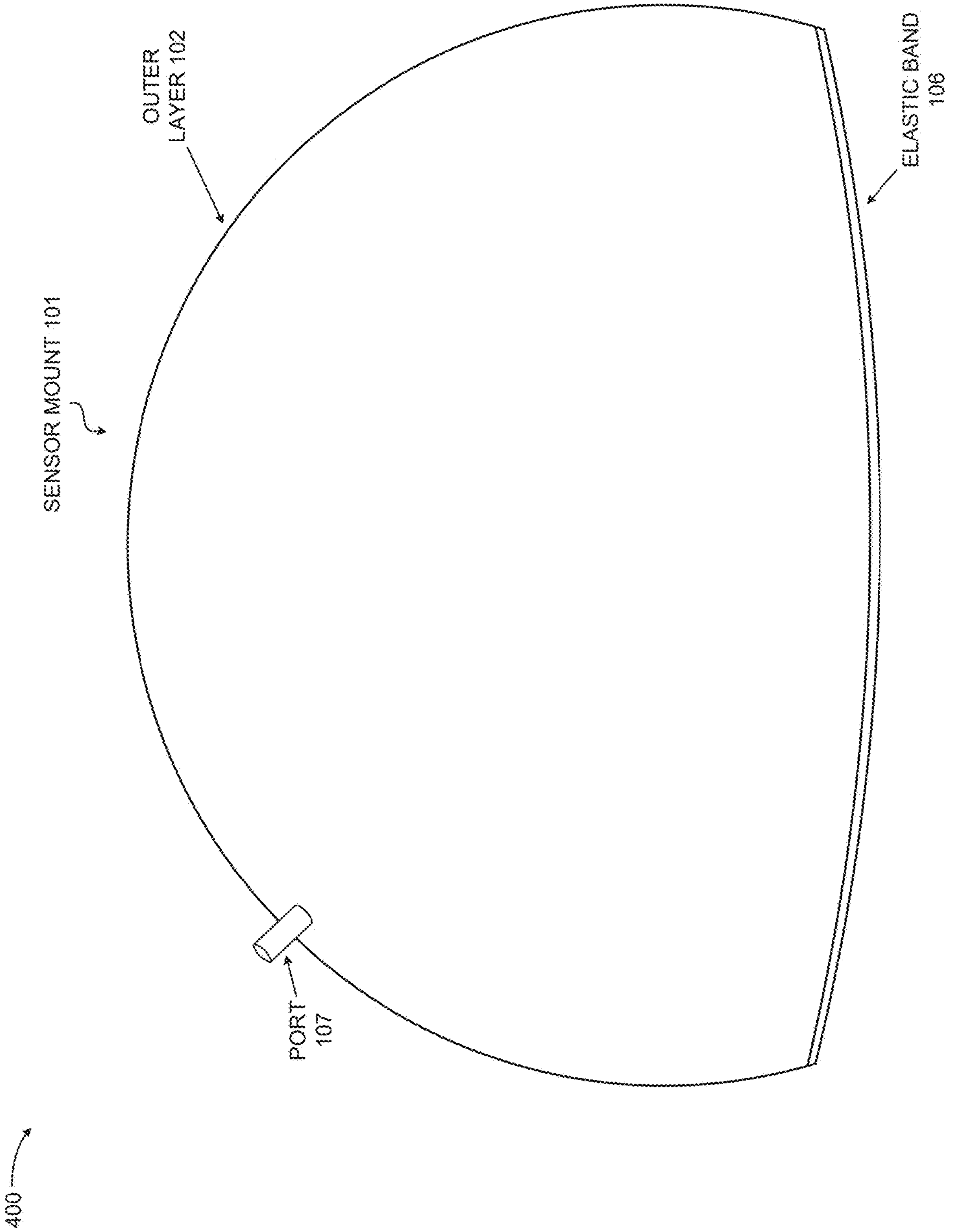
FIG. 4 illustrates an exemplary sensor mount.

FIG. 4 further illustrates view 400. View 400 is representative of an external perspective of sensor mount 101. View 400 comprises sensor mount 101, outer layer 102, elastic band 106, and port 107. The view of filling material 103, inner layer 104, and sensors 105 is obstructed by outer layer 102. In this example, sensor mount 101 is shaped to conform to the human head and may be used in Magnetoencephalography (MEG) applications. However, in other examples sensor mount 101 may comprise a different shape to conform to a different part of the body. For example, in fetal MEG applications of the present technology, sensor mount 101 may be shaped to conform to the head of an infant or small child. For example, in Magnetocardiography (MCG) applications of the present technology, sensor mount 101 may be shaped to conform to the human chest. For example, in fetal MCG applications of the present technology, sensor mount 101 may be shaped to conform to the chest of an infant or small child. For example, in Magnetogastrography (MGG) applications of the present technology, sensor mount 101 may be shaped to conform to the human abdomen. For example, in Magnetomyography (MMG) applications of the present technology, sensor mount 101 may be shaped to conform to the human arm or human leg.

FIG. 5 illustrates process 500. Process 500 is representative of a conformal magnetic imaging process (e.g., conformal MEG) to image neuronal activity in the brain of a target subject. Portions of process 500 may be implemented in program instructions in the context of any of the hardware components, software applications, module components, or other such elements of one or more computing devices.

The operations of process 500 comprise positioning a rigid/flexible MEG cap on the head of a target subject when the MEG cap is in its flexible state (step 501). The operations further comprise pulling a vacuum on the rigid/flexible MEG cap to transition the MEG cap from its flexible state to its rigid state to secure the positions and orientations of the MEG sensors (step 502). The operations further comprise determining the spatial locations of the sensors to localize the sensors (step 503). The operations further comprise measuring the field strength of the magnetic field generated by the target to generate a MEG image (step 504). The operations further comprise releasing the vacuum on the rigid/flexible MEG cap to transition the MEG cap from its rigid state to its flexible state (step 505). The operations further comprise removing the rigid/flexible MEG cap from the head of the target (step 506).

Referring back to FIG. 1, magnetic imaging system 100 includes a brief example of process 500 as implemented by the various hardware and software components that comprise magnetic imaging system 100. The structure and operation of magnetic imaging system 100 may differ in other examples.

In operation, sensor mount 101 is fitted onto the head of target 131 when in its flexible state (step 501). Elastic band 106 constricts sensor mount 101 to press sensors 105 against the scalp of target 131. The position of sensor mount 101 on the head is adjusted until the desired location has been reached. Fluid line 122 is coupled to port 107. For example, fluid line 122 and port 107 may comprise male/female screw couplings to detachably couple fluid line 122 to port 107. Port 107 and fluid line 122 may additionally comprise gaskets, O-rings, seals, and the like to inhibit fluid leakage at the interface between fluid line 122 and port 107.

Valve 108 is set to an open position and pump 121 is activated. For example, an operator may set a ball valve within port 107 to an open position. Alternatively, valve 108 may comprise a spring-loaded valve that opens in response to the creation of a pressure differential from pump 121. Pump 121 pulls air out of the enclosed region in sensor mount 101 through port 107 and fluid line 122 (step 502). The removal of the air creates a low-pressure environment within the enclosed region. The low-pressure environment causes sensor mount 101 to contract reducing the volume of the enclosed region. As the volume of the enclosed region decreases, the particle density of filling material 103 increases causing filling material 103 to undergo a jamming transition—i.e.—transition from a flowing state to a solid state. The solidification of filling material 103 secures the positions and orientations of sensors 105. Valve 108 is closed to maintain the low-pressure environment within the enclosed region of sensor mount 101.

An operator optically scans sensor mount 101 to determine the spatial locations of sensors 105 (step 503). For example, outer layer 102 may comprise fiducial markers that correspond to the embedded positions of sensors 105. An operator may scan the fiducial markers using an imaging device and input the scanned data to controller 111. Controller 111 may execute a localization application to determine the spatial locations for each of sensors 105. It should be appreciated that to perform accurate magnetic field imaging such as in MEG, the spatial locations of sensors 105 must be known to determine the location of magnetic field sources within target 131. Although the example presented herein utilizes optical scanning to localize sensors 105, other sensor localization methods are applicable such as magnetic dipole-based sensor localization, electronic sensor localization, or other types of sensor localization. For example, in the case of dipole localization, a magnetic field source (not illustrated in FIG. 1) may generate a uniform magnetic field that is constant in both direction and magnitude. Sensors 105 measure and report the direction of the uniform magnetic field to controller 111 and controller 111 correlates the measured directions of the uniform magnetic field to orientations for sensors 105. The magnetic field source may then generate a gradient magnetic field that is not constant in both direction and magnitude. Sensors 105 measure and report the field strength of the gradient magnetic field to controller 111 and controller 111 correlates the measured field strengths to distances between individual ones of sensors 105 and the magnetic field source. Controller 111 determines the spatial locations for each of sensors 105 based on the correlated orientations for each of sensors 105, the correlated distances between sensors 105 and the magnetic field source, and the spatial location of the magnetic field source.

Returning to the operation, controller 111 transfers signaling to sensors 105 over cabling 112 that directs sensors 105 to measure the strength of the magnetic field generated by target 131. Sensors 105 receive the signaling and responsively measure the field strength of target 131's magnetic field (step 504). For example, sensors 105 may comprise Optically Pumped Magnetometers (OPMs). The OPMs comprise vapor cells and lasers. The vapor cells in the OPMs may comprise atomic material like alkali atoms and/or Helium atoms. Exemplary alkali atoms include Rubidium atoms. The OPMs measure quantum interactions between the atomic material in the vapor cells and the lasers in the presence of target 131's magnetic field that correlate to the field strength. Sensors 105 generate electronic signals that characterize the field strength of the magnetic field and transfer the electronic signaling that carries the field characterization data over cabling 112 to controller 111. Controller 111 generates a MEG image that depicts the detected neuronal activity in target 131 based on the received magnetic strength data and the spatial locations of sensors 105.

Pump 121 is switched off and/or valve 108 is switched to an open position. Fluid line 122 is detached from port 107 and air flows through port 107 into the enclosed region of sensor mount 101 (step 505). The inflow of air equalizes the pressure within the enclosed region with the ambient pressure. The increase in pressure expands sensor mount 101 thereby increasing the volume of the enclosed region. As the volume of the enclosed region increases, the particle density of filling material 103 decreases causing filling material 103 to undergo a flow transition—i.e.—transition from a solid state to a flowing state. The fluidization of filling material 103 transitions sensor mount 101 to its flexible state. Once in its flexible state, sensor mount 101 is removed from the head of target 131 (step 506).

Figure 6:
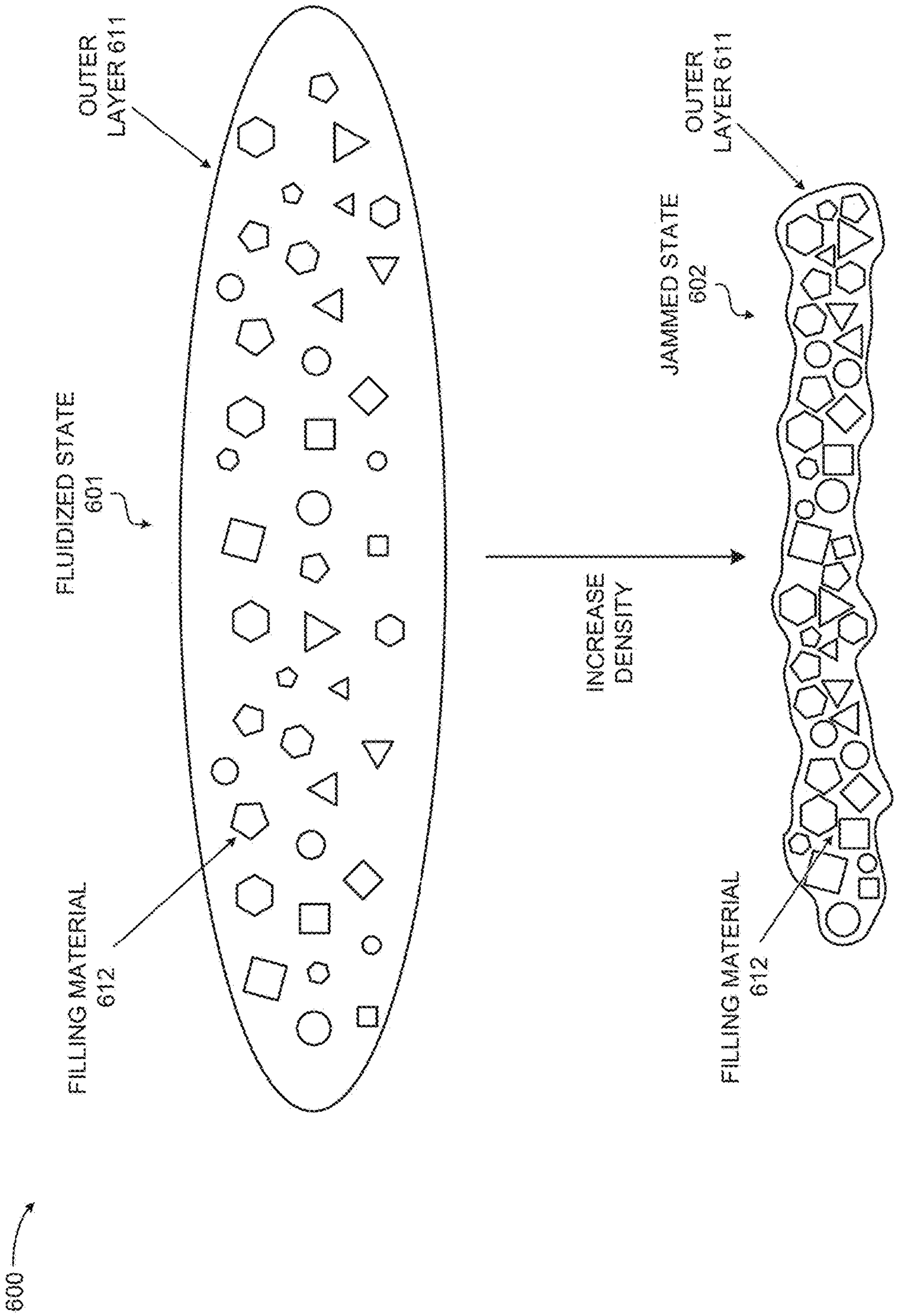
FIG. 6 illustrates an exemplary jamming process.

FIG. 6 illustrates jamming process 600. Jamming process 600 is representative of a particle jamming process in accordance with various embodiments of the present technology. For example, magnetic imaging system 100 may utilize jamming process 600 to transition sensor mount 101 between rigid and flexible states. Jamming process 600 comprises fluidized state 601, jammed state 602, outer layer 611, and filling material 612. Outer layer 611 encloses a volume that comprises filling material 612 and interstitial fluid (e.g., air). Filling material 612 comprises a number of particles with different volumes and geometries. When in fluidized state 601, the particles that comprise filling material 612 can move in a fluidized manner within outer layer 611. For example, filling material 612 may be able to flow like sand. When the density of filling material 612 increases past a critical threshold, fluidized state 601 transitions to jammed state 602. For example, a vacuum may be pulled on outer layer 611 to remove air from the enclosed volume. The removal of air causes a pressure differential between the enclosed volume and the ambient environment. The resulting pressure differential causes the outer surface to contract inward. The inward contraction decreases the volume of the enclosed volume and applies pressure to the individual particles of filling material 612. As the space separating the particles decreases, the particle density of filling material 612 increases. When the particle density of filling material 612 exceeds a critical density, the particles are inhibited from flowing and become locked in place thereby causing filling material 612 to become rigid. For example, the viscosity of filling material 612 may increase with an increase in particle density and filling material 612 may undergo a jamming transition to solidify. The critical density where the jamming transition occurs depends on particle size, particle shape, inter-particle friction, particle compressibility, and/or other physical factors. When jammed, filling material 612 comprises the physical characteristics of a solid mass.

Figure 7:
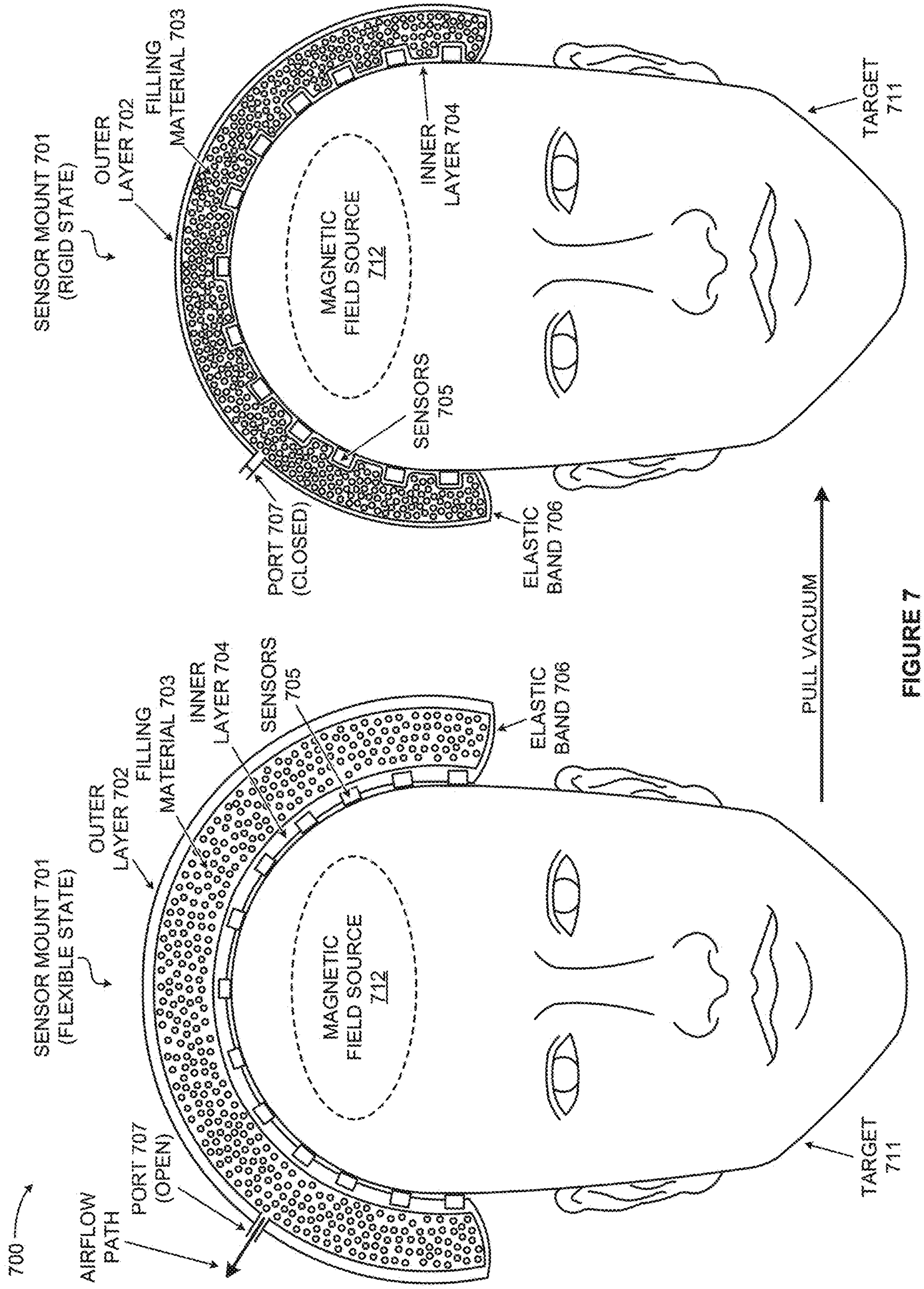
FIG. 7 illustrates an exemplary MEG system.

FIG. 7 illustrates MEG system 700. MEG system 700 comprises an example of magnetic imaging system 100 illustrated in FIG. 1, however magnetic imaging system 100 may differ. MEG system 700 illustrates the operation of a rigid/flexible MEG cap that transitions from a flexible state to a rigid state. MEG system 700 comprises sensor mount 701 and target 711. Sensor mount 701 comprises outer layer 702, filling material 703, inner layer 704, sensors 705, elastic band 706, and port 707. Target 711 comprises magnetic field source 712. Sensor mount 701 is illustrated in a flexible state conformed to the head of target 711 and in a rigid state to secure the positions and orientations of sensors 705. In this example sensor mount 701 comprises a rigid/flexible MEG cap.

In some examples, sensor mount 701 is placed on the head of target 711 when in its flexible state. Sensor mount 701 fits snugly to target 711 and conforms to the surface geometry of the scalp of target 711. Sensor mount 701 places sensors 705 in contact with the scalp of target 711 at spatial locations proximate to magnetic field source 712 in target 711. Elastic band 706 constricts sensor mount 701 to conform sensor mount 701 to the shape of the head. When in the flexible state, the particles that comprise filling material 703 are loosely spaced and are able to flow. When sensor mount 701 is sufficiently positioned on target 711, a vacuum is drawn on sensor mount 701 to remove air from the interior of sensor mount 701 through port 707. The vacuum creates a pressure differential that causes air to flow out of the interior of sensor mount 701. The air flows out of sensor mount 701 along the airflow path as illustrated in FIG. 7.

Sensor mount 701 constricts in response to the decreased internal pressure. The constriction securely presses filling material 703 together. As the particles press together, the particle density of filling material 703 surpasses a critical density and filling material 703 jams forming a rigid structure. The rigid structure of filling material 703 encases sensors 705 to secure the orientation and position of sensors 705. Port 707 can be closed, and the vacuum pump can be turned off, or port 707 can remain open and the pump can continue to operate during magnetic field measurements to maintain the low-pressure environment. When the positions and orientations of sensors 705 are locked in place, MEG system 700 measures the field strength of magnetic field source 712 to image neuronal activity in target 711.

While some examples provided herein are described in the context of magnetic imaging systems like MEG systems that utilize rigid/flexible sensor mounts, it should be understood that the systems and methods described herein are not limited to such embodiments and may apply to a variety of other magnetometry environments and their associated systems. As will be appreciated by one skilled in the art, aspects of the present invention may be embodied as a system, method, apparatus, and other configurable systems. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number, respectively. The word "or" in reference to a list of two or more items, covers all of the following interpretations of the word: any of the items in the list, all of the items in the list, and any combination of the items in the list.

The phrases "in some embodiments," "according to some embodiments," "in the embodiments shown," "in other embodiments," and the like generally mean the particular feature, structure, or characteristic following the phrase is included in at least one implementation of the present technology and may be included in more than one implementation. In addition, such phrases do not necessarily refer to the same embodiments or different embodiments.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as an apparatus claim, other aspects may likewise be embodied as a method claim, or in other forms, such as being embodied in a means-plus-function claim. Any claims intended to be treated under 35 U.S.C. § 112 (f) will begin with the words “means for” but use of the term “for” in any other context is not intended to invoke treatment under 35 U.S.C. § 112 (f). Accordingly, the applicant reserves the right to pursue additional claims after filing this application to pursue such additional claim forms, in either this application or in a continuing application.

What is claimed is:

1. A system comprising:

headgear filled with a filling material, wherein the headgear is in a flexible state when the filling material is under a first pressure and the headgear is in a rigid state when the filling material is under a second pressure.

2. The system of claim 1 wherein:

the filling material comprises a particle matter;

the particle matter is in a fluidized state when under the first pressure and is in a jammed state when under the second pressure; and the headgear is in the flexible state when the particle matter is in the fluidized state and the headgear is in the rigid state when the particle matter is in the jammed state.

3. The system of claim 2 further comprising a pump coupled to the headgear via a fluid line and a port on the headgear; and wherein:

the pump is configured to pull a vacuum on the headgear via the fluid line and the port to transition the particle matter from the fluidized state to the jammed state; and the port comprises a valve configured to open to release the vacuum on the headgear to transition the particle matter from the jammed state to the fluidized state.

4. The system of claim 1 further comprising a sensor attached to the headgear configured to measure a signal generated by a target wearing the headgear.

5. The system of claim 4 wherein the headgear is configured to:

conform to a shape of the target wearing the headgear when the headgear is in the flexible state; and fix a position and orientation of the sensor when the headgear is in the rigid state.

6. The system of claim 4 wherein the sensor is configured to measure a magnetic field generated by neural activity in the target.

7. The system of claim 4 wherein the sensor is configured to measure an electric field generated by neural activity in the target.

8. The system of claim 4 further comprising a controller communicatively coupled to the sensor configured to model neural activity in the target based on a measurement of the signal.

9. The system of claim 8 wherein the controller is configured to generate a Magnetoencephalography (MEG) image to model the neural activity.

10. A method comprising:

establishing a first pressure in a sensor mount to transition the sensor mount from a flexible state to a rigid state;

measuring, by a sensor attached to the sensor mount, a signal generated by a target; and establishing a second pressure in the sensor mount to transition the sensor mount from the rigid state to the flexible state.

11. The method of claim 10 wherein the sensor mount is filled with a particle matter.

12. The method of claim 11 wherein establishing the first pressure in the sensor mount to transition the sensor mount from the flexible state to the rigid state comprises pulling a vacuum on the sensor mount to cause the particle matter to undergo a jamming transition from a fluidized state to a jammed state.

13. The method of claim 11 wherein establishing the second pressure in the sensor mount to transition the sensor mount from the rigid state to the flexible state comprises releasing a vacuum on the sensor mount to cause the particle matter to undergo a jamming transition from a jammed state to a fluidized state.

14. The method of claim 10 further comprising conforming the sensor mount to a shape of the target when in the flexible state.

15. The method of claim 10 wherein establishing the first pressure in the sensor mount to transition the sensor mount from the flexible state to the rigid state comprises fixing a position and orientation of the sensor attached to the sensor mount.

16. The method of claim 10 wherein measuring, by the sensor, the signal generated by the target comprises measuring a magnetic field generated by a biological magnetic field source.

17. The method of claim 10 wherein measuring, by the sensor, the signal generated by the target comprises measuring an electric field generated by a biological electric field source.

18. The method of claim 10 further comprising modeling neural activity of the target based on the signal.

19. The method of claim 18 wherein modeling the neural activity of the target comprises generating a Magnetoencephalography (MEG) image.

20. A Magnetoencephalography (MEG) system comprising:

a MEG cap filled with a particle matter, MEG sensors, a controller, and a pump;

the MEG cap configured to conform to a target's head and mount the MEG sensors, wherein the MEG cap is flexible when the particle matter is in a fluidized state and the MEG cap is rigid when the particle matter is in a jammed state;

the pump configured to pull a vacuum on the MEG cap to transition the particle matter from the fluidized state to the jammed state, wherein the particle matter inhibits changes to orientations and positions of the MEG sensors when in the jammed state;

the MEG sensors configured to measure a magnetic field generated by neural activity of the target and report magnetic field measurements to the controller; and the controller configured to generate a MEG image based on the magnetic field measurements to model neural activity of the target.

* * * * *